(12) United States Patent
Kim et al.

(10) Patent No.: US 8,697,886 B2
(45) Date of Patent: Apr. 15, 2014

(54) DI(AMINOGUANIDIUM) 4,4',5,5'-TETRANITRO-2,2'-BIIMIDAZOLE, AND PREPARATION METHOD THEREOF

(75) Inventors: Jin Seuk Kim, Daejeon-Si (KR); Seung Hee Kim, Daejeon-Si (KR); Hyoun Soo Kim, Daejeon-Si (KR)

(73) Assignee: Agency for Defense Development, Daejeon-Si (KR)

( * ) Notice: Subject to any disclaimer, the term of this patent is extended or adjusted under 35 U.S.C. 154(b) by 238 days.

(21) Appl. No.: 13/365,113

(22) Filed: Feb. 2, 2012

(65) Prior Publication Data

US 2012/0203008 A1    Aug. 9, 2012

(30) Foreign Application Priority Data

Feb. 8, 2011    (KR) .................. 10-2011-0011237

(51) Int. Cl.
*C07D 403/02*    (2006.01)

(52) U.S. Cl.
USPC ....................................... 548/313.4

(58) Field of Classification Search
USPC ....................................... 548/313.4
See application file for complete search history.

(56) References Cited

U.S. PATENT DOCUMENTS 5,395,945 A * 3/1995 Hiskey .................. 548/953

* cited by examiner

*Primary Examiner* — Samantha Shterengarts
(74) *Attorney, Agent, or Firm* — Morrison & Foerster LLP

(57) ABSTRACT

According to the present invention, unstable hydrogen of 4,4',5,5'-tetranitro-2,2'-biimidazole, which is a promising material for insensitive high-performance molecular explosives, may be stabilized by aminoguanidium to provide di(aminoguanidium) 4,4',5,5'-tetranitro-2,2'-biimidazole, thereby solving the hygroscopicity of 4,4',5,5'-tetranitro-2,2'-biimidazole, and enhancing performance and insensitivity thereof.

7 Claims, 2 Drawing Sheets

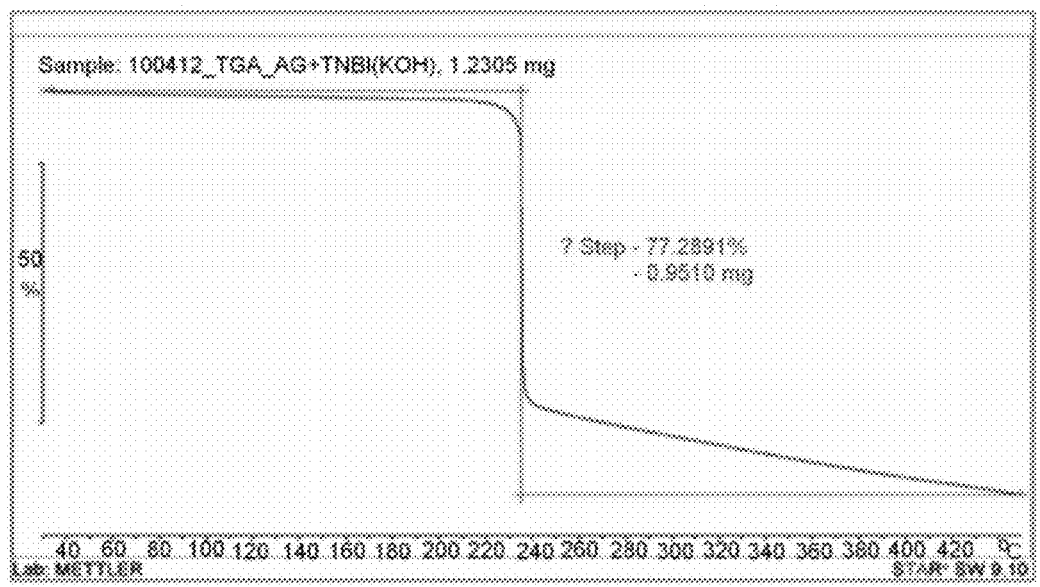

DI(AMINOGUANIDIUM) 4,4',5,5'-TETRANITRO-2,2'-BIIMIDAZOLE, AND PREPARATION METHOD THEREOF

CROSS REFERENCE TO RELATED APPLICATIONS

This application claims priority from Korean Patent Application No. 10-2011-0011237, filed on Feb. 8, 2011, in the Korean Intellectual Property Office, the disclosure of which is incorporated herein by reference in its entirety.

FIELD OF THE INVENTION

The present invention relates to di(aminoguanidium) 4,4',5,5'-tetranitro-2,2'-biimidazole and a preparation method thereof.

BACKGROUND OF THE INVENTION 4,4',5,5'-tetranitro-2,2'-biimidazole (TNBI) represented by the following Chemical Formula 1 is a promising material for insensitive high-performance molecular explosives.

[Chemical Formula 1]

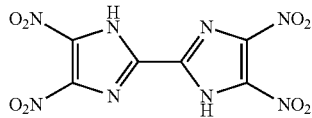

However, the compound is highly hygroscopic, and has a problem of low stability due to unstable hydrogen of the imidazole ring. In case of filling hygroscopic powder into a hermetically sealed body, the property degradation of an explosive may be caused by moisture, thereby deteriorating detonation performance thereof, which is the ultimate goal of the explosive. According to the present invention, hygroscopicity can be solved and thermal stability can be increased, thereby enhancing the performance and insensitivity of an explosive.

SUMMARY OF THE INVENTION

Accordingly, an object of the present invention is to enhance the hygroscopicity and stability of 4,4',5,5'-tetranitro-2,2'-biimidazole, thereby enhancing storage stability.

Another object of the present invention is to provide di(aminoguanidium) 4,4',5,5'-tetranitro-2,2'-biimidazole and a preparation method thereof.

The foregoing object of the present invention can be achieved by the followings.

(1) Di(aminoguanidium) 4,4',5,5'-tetranitro-2,2'-biimidazole represented by the following Chemical Formula 2:

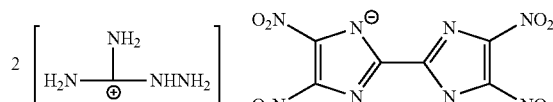

(2) A method of preparing di(aminoguanidium) 4,4',5,5'-tetranitro-2,2'-biimidazole represented by the Chemical Formula 2, including reacting 4,4',5,5'-tetranitro-2,2'-biimidazole to an organic acid or inorganic acid salt of aminoguanidium.

According to the present invention, unstable hydrogen of 4,4',5,5'-tetranitro-2,2'-biimidazole, which is a promising material for insensitive high-performance molecular explosives, may be stabilized by aminoguanidium to solve hygroscopicity and enhance performance and insensitivity. Di(aminoguanidium) 4,4',5,5'-tetranitro-2,2'-biimidazole disclosed by the present invention can completely remove hygroscopicity, which is an inherent characteristic of 4,4',5,5'-tetranitro-2,2'-biimidazole, and enhance insensitivity.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 2 is a thermogravimetric analysis result when aminoguanidium is attached to solve the hygroscopicity of 4,4',5,5'-tetranitro-2,2'-biimidazole.

DETAILED DESCRIPTION OF THE INVENTION

Figure 1:
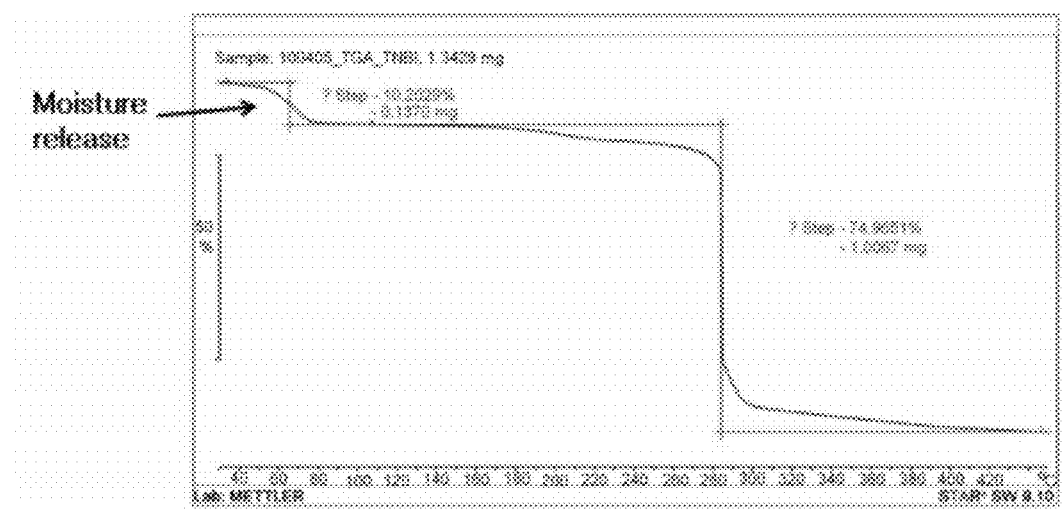
FIG. 1 is a thermogravimetric analysis result of 4,4',5,5'-tetranitro-2,2'-biimidazole, which is a starting material.

The present invention relates to di(aminoguanidium) 4,4',5,5'-tetranitro-2,2'-biimidazole represented by the following Chemical Formula 2.

[Chemical Formula 2]

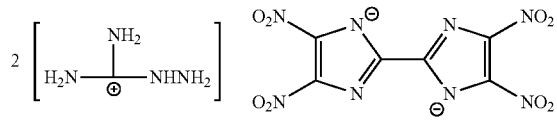

Furthermore, the present invention relates to a method of preparing di(aminoguanidium) 4,4',5,5'-tetranitro-2,2'-biimidazole represented by the Chemical Formula 2, including reacting 4,4',5,5'-tetranitro-2,2'-biimidazole to an organic acid or inorganic acid salt of aminoguanidium.

The organic acid may be an acetic acid, and the inorganic acid may be a sulphuric acid or hydrochloric acid.

The following Reaction Formula 1 illustrates a method of reacting 4,4',5,5'-tetranitro-2,2'-biimidazole to a sulphuric acid salt of aminoguanidium to prepare a compound of the Chemical Formula 2.

[Reaction Formula 1]

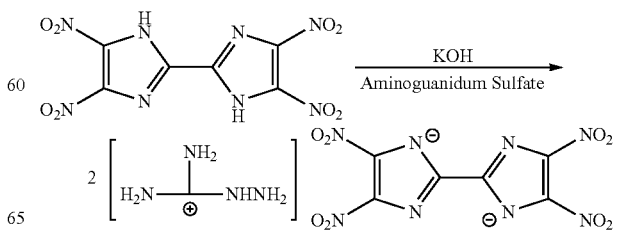

As illustrated in the reaction formula, according to the present invention, 4,4',5,5'-tetranitro-2,2'-biimidazole may be reacted to an organic acid or inorganic acid salt of aminoguanidium under the existence of an a suitable base, for example, potassium hydroxide or sodium hydroxide.

Methanol may be used as a solvent of the reaction, but it may not be limited to this.

At this time, the reaction temperature may be preferably 40 to 70° C., and the reaction time may be preferably 2 to 5 hours.

EXAMPLES

Hereinafter, the present invention will be described in more detail through the examples. However, the present invention will not be limited to the scope of the following examples.

Example 1

Synthesis of 4,4',5,5'-tetranitro-2,2'-biimidazole

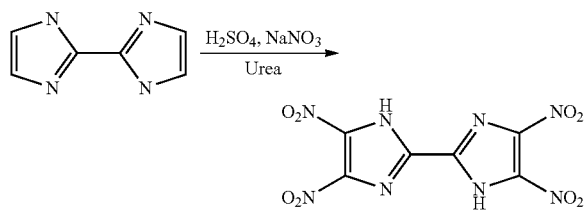

753 mL of about 95% sulphuric acid and 100 g of biimidazole were placed into a 2 L round bottom flask and biimidazole was all dissolved over one hour. When biimidazole had been all dissolved, 4.48 g of urea was placed thereinto as a catalyst, and subsequently, about 60 g of sodium nitrate was slowly injected in a temperature range of 20 to 30° C. Since yellowish brown gas NOx is generated while injecting sodium nitrate, it may be dangerous to inject at a time, and thus sodium nitrate was slowly injected while maintaining a temperature between 20 and 30° C. After injecting all sodium nitrate, the temperature of the reactor was raised to 80° C. to carry out the reaction for 5 hours, thereby completing the reaction. Next, the temperature of the reactor was lowered to 20° C., and a reaction solution was slowly poured into 1 L of ice water. Solid matter extracted from the ice water was filtered out to obtain 142 g of 4,4',5,5'-tetranitro-2,2'-biimidazole in the state of powder (Yield: 60%).

$^1$H-NMR (CDCl3): δ (ppm) 10.58 (br, 2H), $^{13}$C-NMR (CDCl3) δ (ppm): 138.63, 138.24, IR (NaCl): 3600.9 w, 3542.1 w, 1537.1 s, 1484.2 m, 1413.7 m, 1372.5 s, 1325.5

Example 2

Synthesis of di(aminoguanidium) 4,4',5,5'-tetranitro-2,2'-biimidazole 4,4',5,5'-tetranitro-2,2'-biimidazole (10 g, 0.032 mol) and MeOH (200 mL) were placed into a 500 mL reactor and stirred until TNBI was all dissolved while maintaining the temperature of a reaction solution at 60° C. KOH (2 equivalents, 7 g) was dissolved in 100 mL of water and added to a reaction solution. At this time, the solution became a dark yellowish dispersion solution state. When aminoguanidium hydrochloride (2.2 equivalents, 8 g) was added to the mixed solution and then stirred, the solution became darker and darker while occurring ion exchange reaction until it was eventually a dark orange color. Though the ion exchange reaction occurred within several minutes, the solution was sufficiently stirred for 3 to 4 hours to completely accomplish ion exchange. After stirring, the solution was cooled down to normal temperature and filtered out, and then the obtained solid matter was cleaned with ice water. The obtained solid matter was dried to obtain 13.1 g of di(aminoguanidium) 4,4',5,5'-tetranitro-2,2'-biimidazole (Yield: 73%).

IR (neat): v 3423, 3395, 3289, 3096, 1666, 1592, 1520, 1466, 1373, 1303, 1191, 1110, 911, 856, 810, 751

$^1$H NMR (300 MHz, DMSO) δ (ppm) 8.9 (bs, 1H), 7.16 (bs, 4H), 4.72 (bs, 2H); $^{13}$C NMR (75 MHz, DMSO) δ (ppm) 158.91, 143.84, 140.41

Example 3

Thermogravimetric analysis test of 4,4',5,5'-tetranitro-2,2'-biimidazole and di(aminoguanidium) 4,4',5, 5'-tetranitro-2,2'-biimidazole A thermogravimetric analysis was carried out to check whether hygroscopicity was removed (enhanced) when 4,4', 5,5'-tetranitro-2,2'-biimidazole was converted into di(aminoguanidium) 4,4',5,5'-tetranitro-2,2'-biimidazole. For the thermogravimetric analysis, the specimen was placed into a crucible furnace having a scale and then heated at a heating speed of 10° C./min to check whether or not weight reduction due to the removal of a volatile component from the specimen occurred.

FIG. 1 is a thermogravimetric analysis result of 4,4',5,5'-tetranitro-2,2'-biimidazole, and FIG. 2 is a thermogravimetric analysis of di(aminoguanidium) 4,4',5,5'-tetranitro-2,2'-biimidazole. Weight reduction occurred in a temperature range of 50 to 80° C. in FIG. 1 whereas the phenomenon did not occur in FIG. 2, and it was confirmed to show a typical decomposition form of a high-energy molecular explosive that is suddenly decomposed at 220° C. As a result, according to the present invention, hydrogen of 4,4',5,5'-tetranitro-2,2'-biimidazole could be stabilized by aminoguanidium, thereby enhancing the performance and insensitivity of a explosive, as well as solving hygroscopicity.

What is claimed is:

1. Di(aminoguanidium) 4,4',5,5'-tetranitro-2,2'-biimidazole represented by the following Chemical Formula:

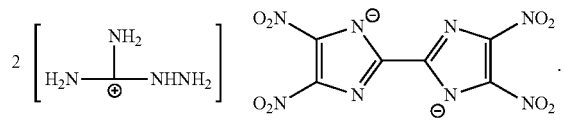

2. A method of preparing di(aminoguanidium) 4,4',5,5'-tetranitro-2,2'-biimidazole of claim 1, comprising:
reacting 4,4',5,5'-tetranitro-2,2'-biimidazole with an organic acid or inorganic acid salt of aminoguanidium.

3. The method of claim 2, wherein the organic acid is an acetic acid, and the inorganic acid is a sulphuric acid or hydrochloric acid.

4. The method of claim 2, wherein the reaction is carried out under the existence of a base.

5. The method of claim 4, wherein the base is potassium hydroxide.

6. The method of claim 2, wherein a methanol is used as a solvent in the reaction.

7. The method of claim 2, wherein the reaction is carried out for 2 to 5 hours at 40 to 70° C.

\* \* \* \* \*